US010244931B2

(12) United States Patent
Kern (10) Patent No.: US 10,244,931 B2
(45) Date of Patent: Apr. 2, 2019

(54) ILLUMINATED OPHTHALMIC INFUSION LINE AND ASSOCIATED DEVICES, SYSTEMS, AND METHODS

(71) Applicant: NOVARTIS AG, Basel (CH)

(72) Inventor: Thomas Kern, Luzern (CH)

(73) Assignee: Novartis AG, Basel (CH)

( * ) Notice: Subject to any disclaimer, the term of this patent is extended or adjusted under 35 U.S.C. 154(b) by 443 days.

(21) Appl. No.: 14/797,763

(22) Filed: Jul. 13, 2015

(65) Prior Publication Data

US 2017/0014023 A1    Jan. 19, 2017

(51) Int. Cl.
| | | |
|---|---|---|
| *A61B 1/07* | (2006.01) | |
| *A61M 5/14* | (2006.01) | |
| *A61F 9/007* | (2006.01) | |
| *A61B 90/30* | (2016.01) | |

(52) U.S. Cl.
CPC .............. *A61B 1/07* (2013.01); *A61F 9/007* (2013.01); *A61M 5/14* (2013.01); *A61B 2090/306* (2016.02)

(58) Field of Classification Search
CPC ..... A61B 90/30; A61B 2090/306; A61B 1/07; A61B 3/0008; A61B 17/0218; A61B 17/0231; A61B 17/3421; A61F 9/0017; A61F 9/0026; A61F 9/007; A61F 9/00736; A61F 9/00763; A61M 5/14; A61M 2205/587

See application file for complete search history.

(56) References Cited

U.S. PATENT DOCUMENTS

| | | |
|---|---|---|
| 3,089,484 A | 5/1963 | Hett |
| 3,093,134 A | 6/1963 | Roehr |
| 3,131,690 A | 5/1964 | Innis et al. |

(Continued)

FOREIGN PATENT DOCUMENTS

| | | |
|---|---|---|
| DE | 19957785 A1 | 6/2000 |
| EP | 0684016 A2 | 11/1995 |

(Continued)

OTHER PUBLICATIONS

International Search Report and Written Opinion of the International Searching Authority, International Application No. PCT/2013/067083, dated Jan. 16, 2014, 9 pages.

(Continued)

*Primary Examiner* — Brandy S Lee (57) ABSTRACT

Systems, apparatuses, and methods of and for an ophthalmic illuminated infusion line are provided. An example ophthalmic illuminated infusion line may include an infusion arrangement having a first flexible elongate member and a flow tube. The first flexible elongate member may have a lumen configured to deliver a fluid to an eye of a patient during a surgical procedure. The flow tube may be sized to penetrate the eye of the patient and deliver the fluid to an interior of an eye to maintain intraocular pressure during a surgical procedure. The ophthalmic illuminated infusion line may also include an optical fiber coupled to the infusion arrangement and configured to penetrate the eye of the patient with the flow tube and transmit light to illuminate the interior of the eye during the surgical procedure at the same time that the flow tube delivers the fluid to the interior of the eye.

3 Claims, 9 Drawing Sheets

Fig. 8

(56) References Cited

U.S. PATENT DOCUMENTS

| | | | |
|---|---|---|---|
| 3,385,553 A | 5/1968 | Braun | |
| 3,439,157 A | 4/1969 | Myles | |
| 3,910,677 A | 10/1975 | Becker et al. | |
| 3,932,022 A | 1/1976 | Henning et al. | |
| 3,981,709 A | 9/1976 | Kondo et al. | |
| 3,990,453 A | 11/1976 | Douvas et al. | |
| 4,168,707 A | 9/1979 | Douvas et al. | |
| 4,200,106 A | 4/1980 | Douvas et al. | |
| 4,248,214 A * | 2/1981 | Hannah | A61M 25/0017 604/20 |
| 4,597,030 A | 6/1986 | Brody | |
| 4,607,622 A | 8/1986 | Fritch et al. | |
| 4,641,912 A | 2/1987 | Goldenberg | |
| 4,678,268 A | 7/1987 | Russo et al. | |
| 4,693,244 A | 9/1987 | Daikuzono | |
| 4,693,556 A | 9/1987 | McCaughan, Jr. | |
| 4,733,933 A | 3/1988 | Pikulski | |
| 4,781,703 A | 11/1988 | Walker et al. | |
| 4,842,390 A | 6/1989 | Sottini et al. | |
| 4,872,837 A | 10/1989 | Issalene et al. | |
| 4,994,047 A | 2/1991 | Walker et al. | |
| 4,995,691 A | 2/1991 | Purcell, Jr. | |
| 5,037,174 A | 8/1991 | Thompson | |
| 5,201,730 A | 4/1993 | Easley et al. | |
| 5,203,353 A | 4/1993 | Easley et al. | |
| 5,217,456 A | 6/1993 | Narciso, Jr. | |
| 5,219,350 A | 6/1993 | Emerson et al. | |
| 5,263,952 A | 11/1993 | Grace et al. | |
| 5,275,593 A | 1/1994 | Easley et al. | |
| 5,312,393 A | 5/1994 | Mastel | |
| 5,351,168 A | 9/1994 | Easley | |
| 5,411,016 A | 5/1995 | Kume et al. | |
| 5,425,730 A | 6/1995 | Luloh | |
| 5,478,338 A | 12/1995 | Reynard | |
| 5,591,160 A | 1/1997 | Reynard | |
| 5,620,639 A | 4/1997 | Stevens et al. | |
| 5,630,809 A | 5/1997 | Connor | |
| 5,651,783 A | 7/1997 | Reynard | |
| 5,667,472 A | 9/1997 | Finn et al. | |
| 5,695,492 A | 12/1997 | Brown | |
| 5,716,320 A | 2/1998 | Buttermore | |
| 5,725,514 A | 3/1998 | Grinblat et al. | |
| 5,754,717 A | 5/1998 | Esch | |
| 5,860,996 A | 1/1999 | Urban et al. | |
| 6,080,143 A | 6/2000 | Connor | |
| 6,206,823 B1 | 3/2001 | Kolata et al. | |
| 6,217,456 B1 | 4/2001 | Narciso, Jr. | |
| 6,387,044 B1 | 5/2002 | Tachibana et al. | |
| 6,428,553 B1 | 8/2002 | Trese | |
| 6,454,744 B1 | 9/2002 | Spohn et al. | |
| 6,939,341 B2 | 9/2005 | Vijfvinkel | |
| 7,766,904 B2 | 8/2010 | McGowan, Sr. | |
| 7,783,346 B2 | 8/2010 | Smith et al. | |
| 7,881,573 B2 | 2/2011 | Eberle et al. | |
| 7,896,838 B2 | 3/2011 | Devega | |
| 7,901,353 B2 | 3/2011 | Vayser et al. | |
| 8,292,434 B2 | 10/2012 | Horvath et al. | |
| 8,496,862 B2 | 7/2013 | Zelkovich et al. | |
| 8,900,139 B2 | 12/2014 | Yadlowsky et al. | |
| 8,968,347 B2 | 3/2015 | McCollam | |
| 8,979,867 B2 | 3/2015 | Peyman | |
| 9,055,885 B2 | 6/2015 | Horvath et al. | |
| 9,066,678 B2 | 6/2015 | Auld et al. | |
| 9,089,364 B2 | 7/2015 | Bhadri et al. | |
| 9,364,982 B2 | 6/2016 | Schaller | |
| 9,402,643 B2 | 8/2016 | Auld et al. | |
| 9,561,085 B2 | 2/2017 | Yadlowsky et al. | |
| 9,839,749 B2 | 12/2017 | Johnson et al. | |
| 9,956,053 B2 | 5/2018 | Diao et al. | |
| 10,016,248 B2 | 7/2018 | Mirsepassi et al. | |
| 10,039,669 B2 | 8/2018 | Heeren | |
| 2001/0056278 A1 | 12/2001 | Nield et al. | |
| 2002/0035425 A1 | 3/2002 | Deguchi et al. | |
| 2002/0123744 A1 | 9/2002 | Reynard | |
| 2004/0215065 A1 | 10/2004 | Setten | |
| 2005/0080384 A1 | 4/2005 | Green, Jr. | |
| 2005/0135776 A1 | 6/2005 | Vijfvinkel | |
| 2005/0154379 A1 | 7/2005 | McGowan et al. | |
| 2005/0245916 A1 | 11/2005 | Connor | |
| 2006/0135973 A1 | 6/2006 | Hawkins et al. | |
| 2006/0211918 A1 | 9/2006 | Lieponis | |
| 2007/0179430 A1 | 8/2007 | Smith et al. | |
| 2007/0255264 A1 | 11/2007 | Hickingbotham | |
| 2008/0147018 A1 | 6/2008 | Squilla et al. | |
| 2008/0179792 A1 | 7/2008 | Kurimoto et al. | |
| 2008/0255545 A1 | 10/2008 | Mansfield et al. | |
| 2009/0030406 A1 | 1/2009 | Hickingbotham | |
| 2009/0131931 A1 | 5/2009 | Lee et al. | |
| 2009/0135280 A1 | 5/2009 | Johnston et al. | |
| 2009/0161384 A1 | 6/2009 | Smith | |
| 2009/0163897 A1 | 6/2009 | Skinner | |
| 2009/0221991 A1 * | 9/2009 | Lieponis | A61B 1/00105 604/540 |
| 2010/0026207 A1 | 2/2010 | Facchini et al. | |
| 2010/0081875 A1 | 4/2010 | Fowler et al. | |
| 2010/0145284 A1 | 6/2010 | Togashi | |
| 2010/0228083 A1 | 9/2010 | Mirza et al. | |
| 2010/0228085 A1 | 9/2010 | Mirza et al. | |
| 2011/0130779 A1 | 6/2011 | Mirza et al. | |
| 2011/0282160 A1 | 11/2011 | Dawson et al. | |
| 2011/0319839 A1 | 12/2011 | Del Vecchio | |
| 2012/0035425 A1 | 2/2012 | Schaller | |
| 2012/0041461 A1 | 2/2012 | McCollam | |
| 2012/0203075 A1 | 8/2012 | Horvath | |
| 2012/0238830 A1 | 9/2012 | Vukeljic et al. | |
| 2012/0283523 A1 * | 11/2012 | Yadlowsky | A61F 9/00763 600/249 |
| 2012/0296173 A1 | 11/2012 | Stocks et al. | |
| 2013/0012783 A1 | 1/2013 | Vayser et al. | |
| 2013/0079598 A1 | 3/2013 | Auld et al. | |
| 2013/0282031 A1 | 10/2013 | Woodward, Jr. et al. | |
| 2014/0100426 A1 | 4/2014 | Barbour | |
| 2014/0121469 A1 | 5/2014 | McCollam et al. | |
| 2014/0210116 A1 | 7/2014 | Schaller | |
| 2014/0357957 A1 | 12/2014 | Bhadri et al. | |
| 2014/0379054 A1 | 12/2014 | Cooper et al. | |
| 2015/0011838 A1 | 1/2015 | Auld et al. | |
| 2015/0011839 A1 | 1/2015 | Auld et al. | |
| 2016/0113722 A1 | 4/2016 | Heeren | |
| 2016/0228207 A1 | 8/2016 | Yadlowsky et al. | |
| 2016/0302878 A1 | 10/2016 | Kern | |
| 2017/0014023 A1 | 1/2017 | Kern | |
| 2017/0014267 A1 | 1/2017 | Kern et al. | |
| 2017/0119491 A1 | 5/2017 | Mirsepassi et al. | |
| 2017/0165114 A1 | 6/2017 | Hallen et al. | |
| 2017/0172694 A1 | 6/2017 | Dos Santos et al. | |
| 2017/0176660 A1 | 6/2017 | Mirsepassi et al. | |
| 2017/0252121 A1 | 9/2017 | Diao et al. | |
| 2018/0055596 A1 | 3/2018 | Johnson | |
| 2018/0132963 A1 | 5/2018 | Diao et al. | |
| 2018/0133057 A1 | 5/2018 | Diao et al. | |
| 2018/0168768 A1 | 6/2018 | Mirsepassi et al. | |
| 2018/0168861 A1 | 6/2018 | Mirsepassi et al. | |

FOREIGN PATENT DOCUMENTS

| | | |
|---|---|---|
| GB | 1207229 A | 9/1970 |
| GB | 1349881 A | 4/1974 |
| JP | H10234665 | 9/1998 |
| JP | 2000245740 | 9/2000 |
| JP | 2001079010 | 3/2001 |
| JP | 2006325973 | 12/2006 |
| JP | 2009519766 | 5/2009 |
| JP | 2009148550 | 7/2009 |
| PL | 166358 | 5/1995 |
| WO | 0139705 A1 | 6/2001 |
| WO | 0248017 A1 | 6/2002 |
| WO | 2004002337 A1 | 1/2004 |
| WO | 2007081474 A2 | 7/2007 |
| WO | 08139982 A1 | 11/2008 |
| WO | 2008139982 | 11/2008 |

(56) References Cited

FOREIGN PATENT DOCUMENTS

| WO | 2009091462 A1 | 7/2009 |
|----|---------------|--------|
| WO | 2012083247 A1 | 6/2012 |

OTHER PUBLICATIONS

PCT International Preliminary Report on Patentability and Written Opinion , Application No. PCT/US2013/67083, Publication No. WO/2014/070664, dated May 5, 2015, 8 pages.
International Search Report for PCT/US2008/086119, Publication No. WO2009/091462, dated Mar. 30, 2009, 2 pages.
PCT International Preliminary Report on Patentability and Written Opinion of the International Searching Authority, International Application No. PCT/US2008/086119, dated Jul. 20, 2010, 7 pages.
PCT International Preliminary Report on Patentability and Written Opinion, PCT/US2011/046942, dated Feb. 12, 2013, 6 pages.
International Search Report for PCT/US2011/046942, dated Nov. 15, 2011, 4 pages.
International Search Report for PCT/US2011/047262, dated Dec. 12, 2011, 2 pages.
Supplementary European Search Report for PCT/US2011/047262, dated Oct. 9, 2013, 8 pages.
Calhoun, The Roto-Extractor in Pediatric Ophthalmology, Tr. Am. Ophth. Soc., vol. LXXIII, pp. 292-305, 1975.
Carron, Fiber Optics in Computer Screens to Save Energy, Feb. 22, 2012, 2 pages retrieved Oct. 29, 2015 from http://phys.org/news/2012-02-fiber-optics-screens-energy.html.
Chalam, et al., Illuminated Curved Vitrectomy Probe for Vitreoretinal Surgery, Ophthalmic Surgery, Lasers and Imaging, Nov./Dec. 2007—vol. 38 Å—Issue 6: 525-526.
Fisher et al., Inexpensive Illuminated Vitrectomy Cutter, The Journal of Retinal and Vitreous Diseases, Dec. 2003, vol. 23, Issue 6, p. 891.
Douvas, Microsurgical Roto-Extractor Instrument for Vitrectomy, Mod. Probl. Ophthal., vol. 15, pp. 253-260 (Karger, Basel 1975).
International Searching Authority, Search Report and Written Opinion of the International Searching Authority, PCT/US2011/046942, dated Nov. 3, 2011, 4 pages.
European Search Report for Application No. 13851516.8, Publication No. EP2861125, Published Apr. 22, 2015, 6 pages.
International Search Report and Written Opinion, PCT/US2015/054426, dated Jan. 8, 2016, 15 pages.
International Search Report and Written Opinion of the International Searching Authority, International Application No. PCT/IB2016/051993, not yet published, Jun. 16, 2016, 11 pages.
"Alcon Global Vitreoretinal Product Catalog" , pp. 25-40, 2014.

\* cited by examiner

ILLUMINATED OPHTHALMIC INFUSION LINE AND ASSOCIATED DEVICES, SYSTEMS, AND METHODS

TECHNICAL FIELD

The present disclosure is directed to ophthalmic surgical devices, systems, and methods. More particularly, but not by way of limitation, the present disclosure is directed to devices, systems, and methods of illuminating an interior of the eye during a surgical procedure with an infusion line that delivers fluid to the interior of the eye.

BACKGROUND

Microsurgical procedures frequently require precision cutting and/or removing of various body tissues. For example, certain ophthalmic surgical procedures require cutting and removing portions of the vitreous humor, a transparent jelly-like material that fills the posterior segment of the eye. The vitreous humor, or vitreous, is composed of numerous microscopic fibrils that are often attached to the retina. Therefore, cutting and removing the vitreous must be done with great care to avoid traction on the retina, the separation of the retina from the choroid, a retinal tear, or, in the worst case, cutting and removal of the retina itself. The cutting and removal of membranes may be particularly difficult in some delicate operations, such as mobile tissue management (e.g., cutting and removal of vitreous near a detached portion of the retina or a retinal tear) and vitreous base dissection. Maintaining proper intraocular pressure and illumination are important so that the difficult surgical maneuvers may be performed successfully.

Microsurgical procedures, such as those in the posterior segment, typically require numerous incisions to access the interior of the eye. Each additional incision may create risk for complications during the procedure and/or recovery. Various tools are inserted through the incisions for use by a user, such as a surgeon or other medical professional, while performing the procedure. For example, a portion of an infusion line may be inserted through one of the incisions. The infusion line delivers fluid to the interior of the eye to maintain intraocular pressure, thereby preventing the eye from collapsing during the surgical procedure. An illuminator, which is a distinct tool from the infusion line, may be inserted through one of the other incisions. The illuminator, such as a chandelier illuminator, illuminates the surgical field. Deploying the illuminator in the surgical field requires time and effort on the user's part to properly place the illuminator and affix the associated cables to keep them stationary. A third tool, a surgical device, may be inserted through yet another of the incisions. The user uses the surgical device, such as a cutting probe, to cut and remove tissue from the eye.

SUMMARY

According to one aspect, the present disclosure describes an ophthalmic infusion line including an infusion arrangement having a first flexible elongate member and a flow tube. The first flexible elongate member may have a lumen configured to deliver a fluid to an eye of a patient during a surgical procedure. The flow tube may be sized to penetrate the eye of the patient and deliver the fluid to an interior of an eye. The ophthalmic infusion line may also include an optical fiber coupled to the infusion arrangement and configured to penetrate the eye of the patient with the flow tube and operable to transmit light to illuminate the interior of the eye during the surgical procedure at the same time that the flow tube delivers the fluid to the interior of the eye.

Another aspect of the present disclosure is directed to an ophthalmic surgical system including a light source, a fluid source, and an illuminated infusion line. The illuminated infusion line may include an infusion arrangement having a flexible elongate member and a flow tube. The flexible elongate member may include a lumen in fluid communication with the fluid source and configured to deliver a fluid from the fluid source to an interior of an eye of a patient during a surgical procedure. The flow tube may be sized to penetrate the eye of the patient and deliver the fluid to the interior of the eye. The system may also include an optical fiber in optical communication with the light source and coupled to the infusion arrangement. The optical fiber may be configured to transmit light from the light source to illuminate the interior of the eye during the surgical procedure.

A third aspect of the disclosure is directed to a method of performing an ophthalmic surgical procedure. The method may include creating one or more incisions in the sclera of an eye to access an interior of the eye and inserting a flow tube of an illuminated infusion line through a first incision of the one or more incisions. The illuminated infusion line may include an infusion arrangement having the flow tube and a flexible elongate member. The flexible elongate member may have a lumen in fluid communication with a lumen the flow tube and may be configured to carry fluid. The illuminated infusion line may also include an optical fiber coupled to the infusion arrangement and configured to transmit light. The method may also include delivering the fluid to the interior of the eye through the flow tube of the infusion line and illuminating, at the same time as delivering the fluid, the interior of the eye using the light transmitted by the optical fiber during the ophthalmic surgery.

The various aspects of the disclosure may include one or more of the following features. The optical fiber may be disposed within the first flexible elongate member. The optical fiber may be separate and apart from the first flexible elongate member. The infusion arrangement may include a second flexible elongate member and the optical fiber may be disposed within the second flexible elongate member. The infusion arrangement may include a coupling joint connecting the first and second flexible elongate members. A lumen of the flow tube may be in fluid communication with the lumen of the first flexible elongate member. The optical fiber may be disposed within the flow tube. The optical fiber may be coupled to an exterior of the flow tube. The flow tube may include a groove on an exterior surface thereof. The groove may be sized and shaped to receive the optical fiber. The optical fiber may be disposed within the groove. The ophthalmic infusion line may further include a protection layer surrounding the optical fiber. At least one of the light source and the fluid source may be integrated into a surgical console. The optical fiber may be disposed within the flexible elongate member. The light source may be configured to transmit at least one of laser light, white light, red light, blue light, green light, visible light, near infrared light, or infrared light.

The various aspects of the disclosure may also include one or more of the following features. The flexible elongate member may be coupled to a fluid source. The optical fiber may be coupled to a light source. The flexible elongate member may be coupled to a surgical console. The optical fiber may be coupled to the surgical console. The plurality of incisions may include two incisions. A surgical device may be inserted through a second incision of the one or more incisions. The surgical device may be used to perform a treatment on the eye while the interior of the eye is illuminated with light transmitted by the optical fiber. Shadows generated in the interior of the eye may be minimized while illuminating the interior of the eye. Delivering the fluid to the interior of the eye through the flow tube of the infusion line may include delivering the fluid to the interior of the eye through the flow tube of the infusion line to maintain intraocular pressure during the ophthalmic surgical procedure.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate implementations of the systems, devices, and methods disclosed herein and together with the description, serve to explain the principles of the present disclosure.

These figures will be better understood by reference to the following detailed description.

DETAILED DESCRIPTION

For the purposes of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In addition, this disclosure describes some elements or features in detail with respect to one or more implementations or Figures, when those same elements or features appear in subsequent Figures, without such a high level of detail. It is fully contemplated that the features, components, and/or steps described with respect to one or more implementations or Figures may be combined with the features, components, and/or steps described with respect to other implementations or Figures of the present disclosure. For simplicity, in some instances the same or similar reference numbers are used throughout the drawings to refer to the same or like parts.

The present disclosure describes illumination of tissues within the eye. Particularly, the present disclosure relates generally to devices, systems, and methods for illuminating the interior of the eye during a surgical procedure using an illuminated infusion line. An optical fiber configured to transmit light may be integrated in the infusion line and provide illumination within the eye. Illumination provided by the optical fiber integrated into the infusion line may be similar to that provided by a standalone illuminator but without requiring a separate incision in the eye and a separate illumination instrument. For example, the optical fiber may transmit wide-angle, white light in order to illuminate a surgical field. In other instances, the optical fiber may provide other light frequencies at other angular spreads in order to illuminate the surgical field. The illuminated infusion line provides light in the surgical field at the same time that it delivers fluid into the eye, such as to maintain intraocular pressure within the eye.

The devices, systems, and methods of the present disclosure provide numerous advantages. Incorporating illumination into the infusion line, which is used to introduce fluid into the eye and, thereby, to maintain intraocular pressure during ophthalmic surgical procedures, allows the total number of instruments being introduced within the eye to be minimized. That is, an independent illuminator may be eliminated as a result of the illumination provided by the infusion line. Further, the elimination of a separate illumination device reduces the number of incisions that are needed within the eye during the surgical procedures. This reduction in incisions reduces the risk of complication during the surgical procedures, reduces the risk of post-operative complication, reduces the time to complete the surgical procedure, and simplifies the surgical set up associated with the surgical procedure.

Also, an illuminated infusion line within the scope of the disclosure may provide bright, white, wide-angle light over the course of an entire surgical procedure because the infusion line is generally the first component positioned at the start of the procedure and the last component removed at the end of the procedure. Further, the optical fiber, which is in optical communication with a light source, may be implemented within the same cable coupling the infusion line and a fluid source. This reduces the number of cables near the patient's eye that need to be affixed. Further, because an infusion line would require coupling to a fluid source, incorporating an optical fiber that would require coupling to a light source would not add a substantial amount of set-up time during the surgery. Additionally, the infusion line may be positioned within the eye at any desired position. Particularly, the illuminated infusion line may be positioned at a location that would minimize the presence of shadows within the eye. Thus, an advantageous position for the infusion line may be selected to minimize shadows within the surgical field compared to when instruments are inserted through illuminated trocar cannulas. In some instances, the position of the illuminated infusion line may be selected during the course of a surgical procedure. Illumination may also promote the safe detection and control of the position of the infusion line.

Figure 1:
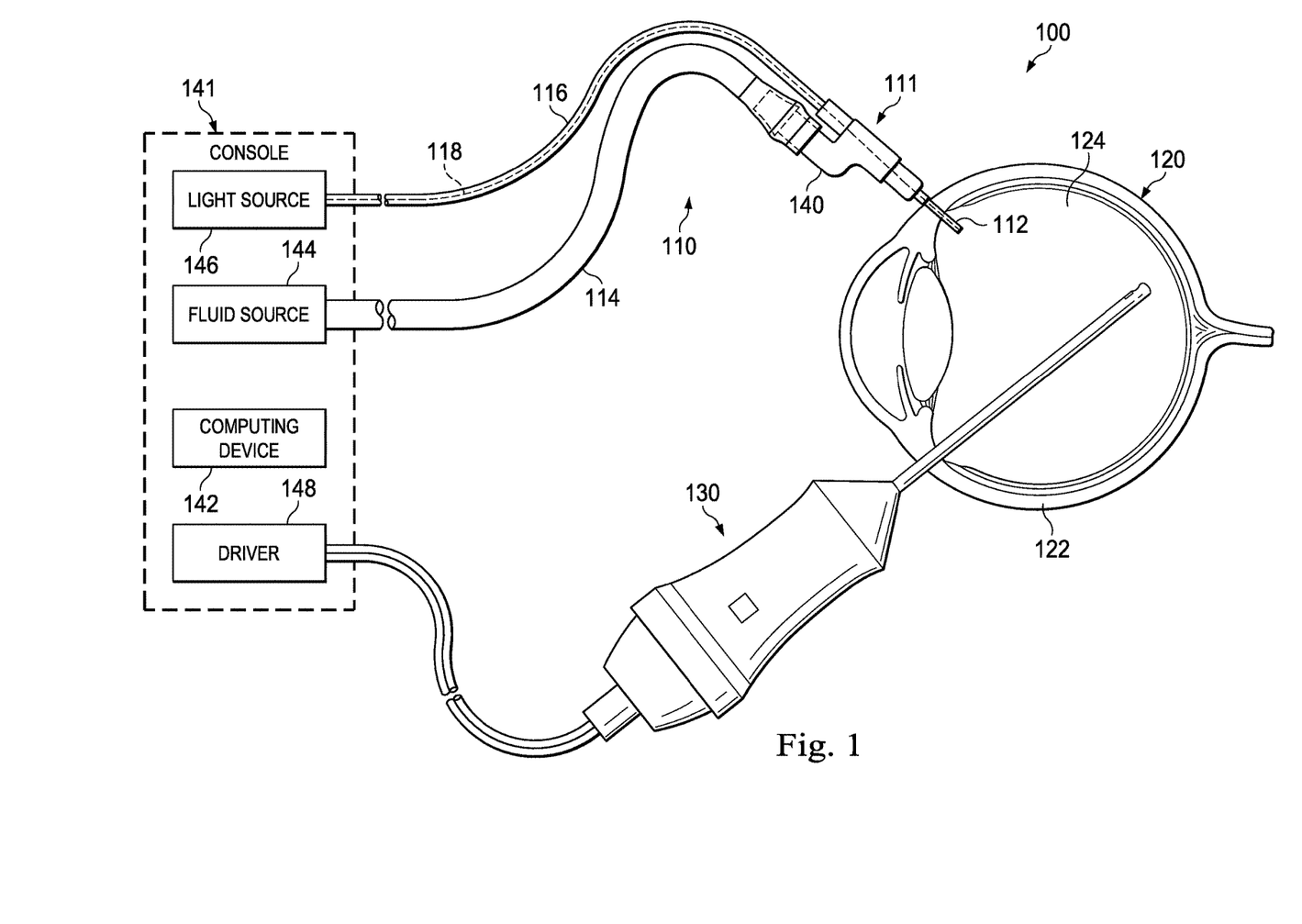
FIG. 1 is an illustration of an example ophthalmic surgical system including an example illuminated infusion line in situ in an eye.

FIG. 1 illustrates an example ophthalmic surgical system 100. The system 100 may be used in various ophthalmic procedures, such as an anterior segment procedure, a posterior segment procedure, a vitreoretinal procedure, a vitrectomy procedure, a cataract procedure, and/or other desired procedures. The system 100 includes an illuminated infusion line 110, an optical fiber 118, a surgical instrument 130, and a console 141. FIG. 1 shows the example illuminated infusion line 110 in situ in an eye 120. The illuminated infusion line 110 has an infusion arrangement 111 that may include a flow tube 112, a flexible elongate member 114, a flexible elongate member 116, and a coupling joint 140. The coupling joint 140 is described in greater detail below with reference to other figures herein.

The flow tube 112 is inserted through the sclera 122 of the eye 120 and into the posterior segment 124 of the eye 120. In some implementations, the flow tube 112 has a generally cylindrical shape. In other implementations, the flow tube 112 may be any suitable size and/or shape to penetrate or pass into an interior of the eye 120. In some implementations, the flow tube 112 is formed of a rigid material. For example, rigid metal or polymeric materials may be suitable. Some flow tube implementations use stainless steel and/or other desired or suitable material(s). The flow tube 112 is configured to deliver fluid into the posterior segment 124, such as to maintain intraocular pressure within the eye 120 during the surgical procedure.

The flexible elongate member 114 may be any medical-grade tubing, such as silicone, plastic, elastomeric, and/or other desired or suitable tubing. The flexible elongate member 114 may have a generally cylindrical shape or other desired size(s) and/or shape(s) in various implementations. The flexible elongate member 114 is in fluid communication with the flow tube 112 through the coupling joint 140. The flexible elongate member 114 is also in fluid communication with a fluid source 144. A lumen of the flexible elongate member 114 carries fluid from the fluid source 144 to the coupling joint 140 and to a lumen of the flow tube 112, which delivers the fluid into the interior of the eye 120. The fluid source 144 is configured to output any suitable or desired liquid(s) and/or gas(es) to flexible elongate member 114. The fluid source 144 may be part of and/or otherwise in fluid communication with a fluidics cassette or fluidics subsystem of the surgical system 100. For example, the fluid source 144 may include a reservoir of fluid or a mechanism, such as a pump or compressor, for example, in fluid communication with such a reservoir. In some implementations, the fluid source 144 provides an irrigation fluid, such as water, saline, or a balanced salt solution for delivery into the interior of the eye 120. For example, in some instances, an irrigation fluid such as BSS® Irrigating Solution and/or BSS PLUS® Irrigating Solution produced by Alcon of 6201 South Freeway, Fort Worth, Tex. 76134.

The optical fiber 118 also interfaces, extends through, or cooperates with the coupling joint 140 to transmit light to the interior of the eye 120 to illuminate the surgical field at the same time as the flow tube 112 delivers the fluid to the interior of the eye 120. As such, in some implementations, at least a portion of the optical fiber 118 extends through the sclera 122 and into the posterior segment 124. Any desired or suitable optical fiber 118 capable of transmitting light may be utilized. In some implementations, the optical fiber 118 may have a relatively small diameter, enabling the optical fiber 118 to be disposed within, coupled to, or otherwise cooperate with the fluid flow tube 112.

As shown in FIG. 1, the optical fiber 118 is coupled to a light source 146. The light source 146 may be configured to output any desired or suitable type of light. For example, the slight source 146 may be operable to output any desired frequency or frequencies of light and any intensity of light. The light source 146 may include an incandescent light bulb, a halogen light bulb, a metal halide light bulb, a xenon light bulb, a mercury vapor light bulb, a light emitting diode (LED), combinations thereof, and/or other light sources. For example, the light source 146 may be a laser source configured to transmit laser light. The light source 146 may be configured to transmit white light, red light, blue light, green light, visible light, near infrared light, and/or infrared light. In some implementations, the optical fiber 118 of the illuminated infusion line 110 is configured to provide illumination to a wide field of view within the eye. In this manner, another source of illumination for the surgical procedure may be avoided as the illuminated infusion line 110 may be operable to illuminate the entire surgical field.

The flexible elongate member 116 may be a cover, sheath, or other protector for the optical fiber 118. The flexible elongate member 116 may be formed of any medical-grade tubing, such as plastic, elastomeric, and/or other desired or suitable tubing. In some implementations, the flexible elongate member 166 may be formed of a silicone material. In the illustrated implementation, the diameter of the flexible elongate member 116 is less than the diameter of the flexible elongate member 114. In other implementations, the diameter of the flexible elongate member 116 may be equal to or larger than the flexible elongate member 114. The flexible elongate member 116 may have a generally cylindrical shape. In other implementations, the flexible elongate member 116 may have other desired size(s) and/or shape(s). The optical fiber 118 may be disposed within a lumen of the flexible elongate member 116. In some implementations, the optical fiber 118 may be freely movable within the lumen of the flexible elongate member 116. In other implementations, the optical fiber 118 may be directly or indirectly coupled to a lumen wall, such as by mechanical attachment, adhesive, and/or other desired or suitable coupling mechanism. In some implementations, the flexible elongate members 114 and 116 may be coupled and/or proximate to one another, so as to make it easier to handle the illuminated infusion line 110. For example, the flexible elongate members 114 and 116 may be joined by a single sheath such that a user (e.g., surgeon, nurse, technician, other medical professional, etc.) only handles one tube, as opposed to the two flexible elongate members 114 and 116 separately. In still other implementations, the flexible elongate members 114 and 116 may be integrally formed. For example, the integrally formed flexible elongate members 114 and 116 may be a flexible member that defines a first lumen for passing a fluid from the fluid source 144 and a second passage for passing the optical fiber 118. In some instances, the first and second lumens may be fluidically isolated from each other such that fluid in one of the lumens in unable to enter the other of the lumens. In other instances, the first lumen may pass through and be fluidically isolated from the second lumen or vice versa.

The optical fiber 118 may be coupled to or cooperatively attached with the infusion arrangement 111 of the illuminated infusion line 110. In some implementations, the optical fiber 118 may pass through the coupling joint 140 and may be disposed within the flow tube 112, as shown in FIG. 1. In some instances, the optical fiber 118 may be disposed in a passage of the flow tube 112 separate from the lumen used to pass the irrigation fluid into the eye 120. In other instances, the optical fiber 118 may extend through the lumen of flow tube 112. In some instances, the optical fiber 118 is freely movable within the flow tube 112, such as in the lumen thereof or a separate compartment or passage. In still other instances, the optical fiber 118 may be directly or indirectly coupled to an inner wall of the flow tube 112, such as by mechanical attachment, adhesive, and/or other desired or suitable coupling mechanism. In some instances, the inner wall may define the lumen of the flow tube 112. In some implementations, the optical fiber 118 may be coupled to an exterior of the flow tube 112, as shown in and described with respect to FIGS. 8 and 8A below. In such implementations, the optical fiber 118 may be directly or indirectly coupled to an outer wall of the flow tube 112, such as by mechanical attachment, adhesive, and/or other desired or suitable coupling mechanism.

FIG. 1 shows the illuminated infusion line 110 in use during a surgical procedure. Accordingly, in this example, the surgical system 100 includes a surgical instrument, referenced herein as a surgical device 130, for treating an ophthalmic condition. The surgical device 130 may be inserted through another incision in the sclera 122 and extend into the posterior segment 124. A user may utilize the surgical device 130 to perform cutting, manipulation, removal, and/or other surgical tasks on tissue at the target surgical site. The light transmitted by the optical fiber 118 illuminates the surgical field such that the user may see the tissue that, for example, is of interest to a user or being targeted by the surgical device 130. The surgical device 130 illustrated in FIG. 1 is a vitrectomy probe. However, it is understood that the surgical device 130 may be any desired or suitable surgical instrument. In some implementations, the surgical device 130 includes a cutting probe, a phacoemulsification probe, shears, forceps, scissors, spatula, a pic, or other type of medical instrument or device. The surgical device 130 may be operatively coupled to a driver 148, such as pneumatic, electric, piezoelectric, and/or other suitable driver. The driver 148 may be utilized to actuate the surgical device 130.

Depending on the implementation, the console 141 may include the fluid source 144, the light source 146, and/or the driver 148. The console 141 may also include a computing device 142 communicatively coupled to the fluid source 144, the light source 146, and/or the driver 148. The computing device 142 may include any desired processing architecture, such as a processor, memory, and/or other suitable components. The computing device 142 may generate and transmit control signals to the fluid source 144, the light source 146, and/or the driver 148 for operation of the illuminated infusion line 110 and/or the surgical device 130. The computing device 142 may generate and transmit the control signals in response to user inputs received via one or more user input devices communicatively coupled to the computing device 142. For example, the computing device 142 may transmit control signals to activate or deactivate fluid flow and/or generate light to be transmitted to the illuminated infusion line 110. The computing device 142 may also transmit signals to control parameters associated with fluid flow and/or illumination. For example, the user may select the wavelength of light transmitted by the light source 146, the flow rate of fluid provided by the fluid source 144, the driving frequency of the driver 148, among other parameters. The computing device 142 may receive data associated with the surgical field, such as intraocular pressure, amount of time the eye 120 has been exposed to a particular wavelength of light, etc. The computing device 142 may generate and transmit control signals based on the received data.

In the illustrated implementation of FIG. 1, the computing device 142, the fluid source 144, the light source 146, and/or the driver 148 are integrated and/or disposed in the surgical console 141. As such, the flexible elongate members 114 and 116 may be directly or indirectly coupled to the surgical console 141 to establish fluid and optical communication with the fluid source 144 and the light source 146, respectively. In other implementations, the computing device 142, the fluid source 144, the light source 146, and/or the driver 148 may be separate and/or remote from the console 141. For example, fluid communication may be established by directly or indirectly connecting the flexible elongate member 114 to the fluid source 144. Similarly, optical communication may be established by directly or indirectly connecting the flexible elongate member 116 and/or the optical fiber 118 to the light source 146.

Figure 2:
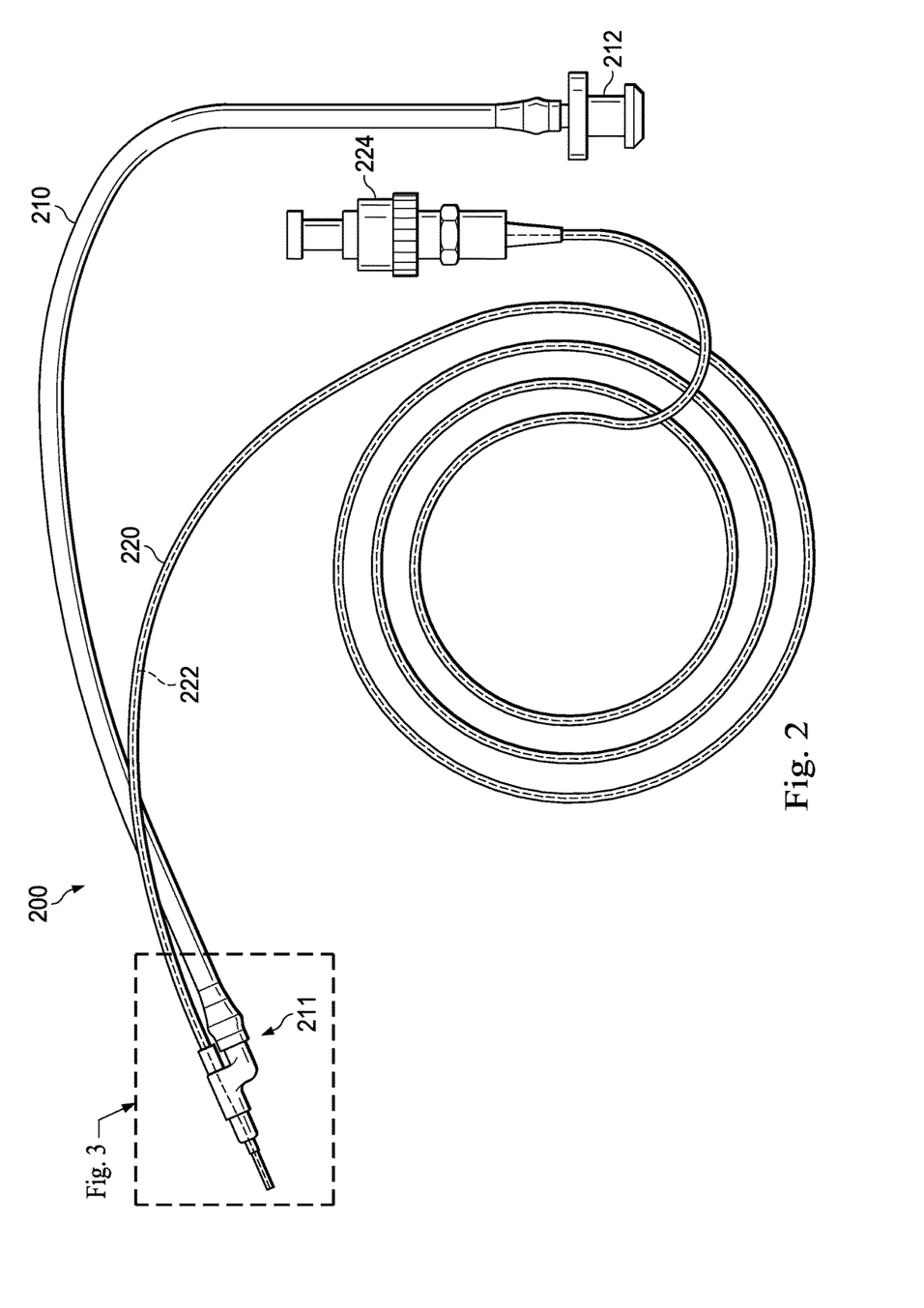
FIG. 2 shows an example illuminated infusion line in situ in an eye.

FIG. 2 shows an exemplary illuminated infusion line 200 with an infusion arrangement 211 that includes a flexible elongate member 210 and an optical fiber 222 disposed within a flexible elongate member 220. The flexible elongate member 210 and/or the flexible elongate member 220 with the optical fiber 222 may each be formed as single-segment flexible elongate members, or may be formed of a plurality of single-segment flexible elongate members joined together in series to achieve any desired length. Accordingly, a single-segment flexible elongate member 220 with a single-segment optical fiber 222 may be long enough to be directly coupled to the light source, such as one similar to the light source 146 shown in FIG. 1, via a connector 224. Similarly, a single-segment flexible elongate member 210 may be long enough to be directly coupled to a fluid source, such as one similar to the fluid source 144 shown in FIG. 1, via connector 212. Alternatively, the flexible elongate member 210, the flexible elongate member 220, and/or the optical fiber 222 may include multiple segments, such as two, three, four, or more segments aligned and coupled in series to achieve desired lengths respectively thereof. The example in FIG. 2 shows the flexible elongate member 210 as being relatively short compared to the longer flexible elongate member 220. In some instances, one or more additional segments may be coupled to the flexible elongate member 210 at a connector 212 to achieve a desired length. In other implementations, the flexible elongate members 210 and 220 may be the same length. In still other implementations, the flexible elongate member 210 may be longer than the flexible elongate member 220.

Figure 3:
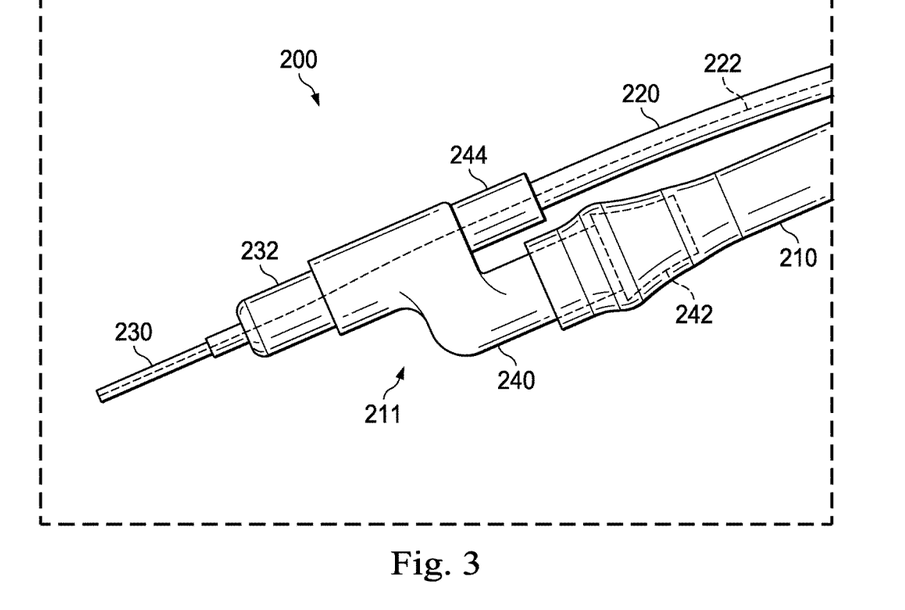
FIG. 3 shows an example illuminated infusion line.
Figure 4:
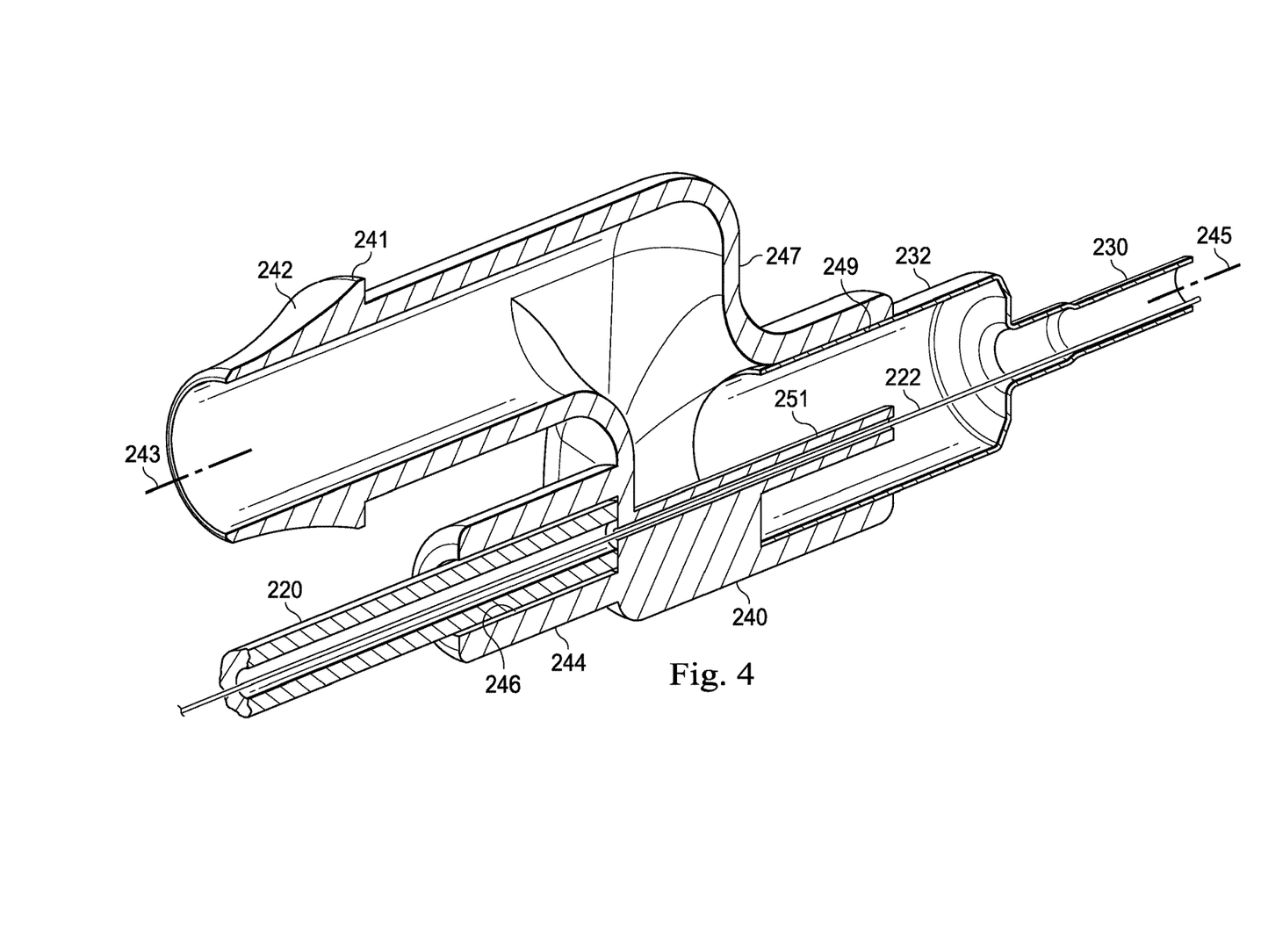
FIG. 4 shows a distal portion of the illuminated infusion line of FIG. 3.

FIGS. 3 and 4 show a distal portion of the example illuminated infusion line 200. FIG. 3 provides a side view of the distal portion, while FIG. 4 is a perspective cross-sectional view of the distal portion of the illuminated infusion line 200. The infusion line 200 includes the infusion arrangement 211, which includes a flow tube 230 that is configured to be inserted into the eye, the flexible elongate members 210 and 220, a rigid member 232, and a coupling joint 240. The flow tube 230 extends from the coupling joint 240, and in some implementations, the flow tube 230 may be integrally formed with the rigid member 232. In other implementations however, the flow tube 230 may be separately formed from but attached to and supported by the rigid member 232. The rigid member 232 may be a hollow body that provides rigidity and stabilizing support for the flow tube 230. As illustrated in FIG. 4, the rigid member 232 is received within a bore 249 of the coupling joint 240. For example, the rigid member 232 may be secured within the bore 249 via a press fit, interference fit, and/or any other coupling manner. For example, the rigid member 232 may be exclusively or partially secured within the bore 249 via an adhesive, welding, threaded coupling, or other joining manner. Other loose fits may also be used, and the rigid member 232 may be attached via an adhesive or other structure to the coupling joint 240. In some implementations, the flow tube 230 may be a portion of the rigid member 232 having the smallest radius. As such, the flow tube 230 may be utilized to penetrate tissue during a surgical procedure. Depending on the implementation, the coupling joint 240 and the rigid member 232 may be formed of the same material or may be formed of different materials. In some examples, the coupling joint 240 may be formed of a plastic or polymeric material, while the rigid member 232 is formed of a metal material.

The coupling joint 240 joins the flexible elongate members 210 and 220. As shown in FIGS. 3 and 4, the coupling joint 240 includes a proximal connector 242 and a proximal connector 244. The flexible elongate member 210 connects to the proximal connector 242 to establish fluid communication with the coupling joint 240 and the flow tube 230. In that regard, the flexible elongate member 210 may be disposed around or over the proximal connector 242 and over a lip 241 of the proximal connector 242 in a manner that prevents the flexible elongate member 210 from becoming unintentionally uncoupled from the coupling joint 240. For example, an outer diameter of the lip 241 may be larger than an internal diameter of a passage formed in the flexible elongate member 210. Thus, the distal end of flexible elongate member 210 is expanded when passed over the lip 241, forming an interlocking connection to maintain a distal end of the flexible elongate member 210 on the proximal connector 242. In some implementations, the flexible elongate member 210 may be removably coupled to the coupling joint 240, while, in other implementations, the flexible elongate member 210 is permanently attached.

The flexible elongate member 220 may be connected to the proximal connector 244 such that the optical fiber 222 extends through the coupling joint 240 and the flow tube 230. In the example shown, the flexible elongate member 220 is received within the bore 246 defined by the proximal connector 244. In some implementations, the flexible elongate member 220 is removably coupled to the coupling joint 240. In some implementations, the flexible elongate member 220 may be secured within the bore 246 via a press fit, interference fit, and/or any other coupling manner. For example, the distal end of the flexible elongate member may be exclusively or partially secured within the bore 249 via an adhesive, welding, threaded coupling, or other joining manner. Other loose fits may also be used, and the flexible elongate member 220 may be attached via an adhesive or other structure to the coupling joint 240.

In use, infusion fluid from the flexible elongate member 210 enters the coupling joint 240 and continues through the rigid member 232 and the flow tube 230 and into a patient's eye. In some instances, the optical fiber 222 may be in contact with the fluid within the coupling joint 240, the rigid member 232, and/or the flow tube 230. The diameter of the optical fiber 222 may be small enough such that the optical fiber 222 does not obstruct the flow of fluid out of the flow tube 230 and into the eye.

The infusion arrangement 211 of the illuminated infusion line 200 may employ any suitable or desired mechanical, fluid, and/or optical coupling among the coupling joint 240, the flow tube 230, the optical fiber 222, the flexible elongate member 210, and/or the flexible elongate member 220. In implementations like those illustrated in FIGS. 3 and 4 in which the optical fiber 222 is not disposed within the same flexible elongate member that carries fluid (e.g., the flexible elongate member 210), the coupling joint 240 may be any suitable size and shape to join the optical fiber 222 and the flexible elongate member 210. In that regard, the optical fiber 222 may be disposed within the flexible elongate member 220. The coupling joint 240 may be sized and shaped to permit the optical fiber 222 to extend through the flow tube 230 in a generally linear manner. In the example shown, the coupling joint 240 includes a guide 251 formed therein. The guide 251 structurally supports and maintains the optical fiber 222 in a linear arrangement to ensure that the optical fiber 222 avoids being undesirably bent and potentially damaged. In this example, the guide 251 is disposed within the coupling joint 240 in alignment with the proximal connector 244 and parallel to an axis 245 formed by the flow tube 230. However, the scope of the disclosure is not so limited. Rather, the guide 251 may have other orientations relative to the proximal connector 244 or other parts of the coupling joint 240.

The path of the fluid flow from the flexible elongate member 210 through the coupling joint 240 may be linear or may be non-linear. In the implementation shown in FIGS. 3 and 4, fluid may flow into the coupling joint 240 along an axis 243, to a curved transition zone 247, and along the axis 245. Thus, the axis 243 may be offset from axis 245. Here, the flow tube 230 and the optical fiber 222, as well as the axis 243, are positioned generally parallel to the axis 245 in the illustrated implementation of FIG. 4. In some implementations, the coupling joint 240 may be omitted, such as when the optical fiber is disposed within the flexible elongate member that carries fluid (as shown, for example, in FIG. 5 described below). In such implementations, the coupling joint 240 may be eliminated because the optical fiber and the fluid flow are generally aligned along the same axis. In some instances, the coupling joint 240 may be single-use or disposable component. In other instances the coupling joint 240 may be reusable. For example, in some instances, the coupling joint 240 may be reused after being sterilized.

Figure 5:
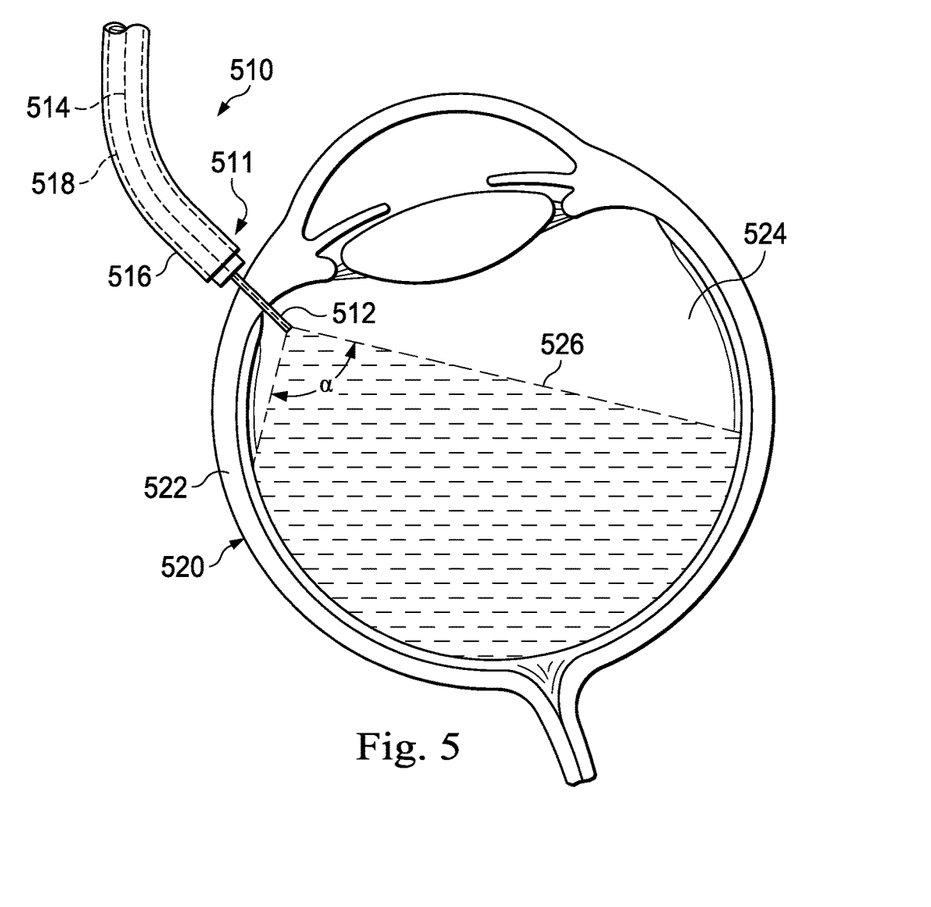
FIG. 5 shows a cross-sectional view of a distal portion of the illuminated infusion line of FIG. 3.
Figures 6, 6A:
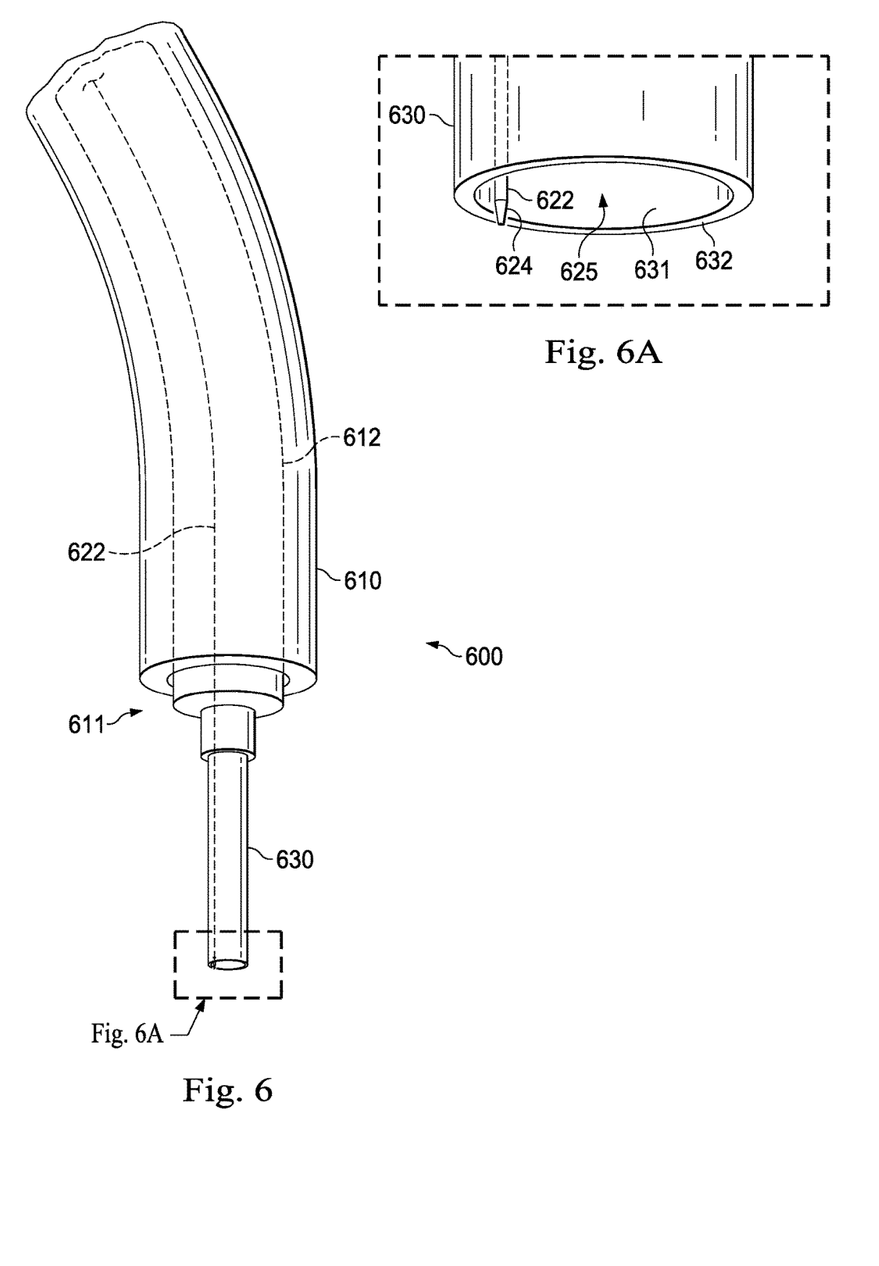
FIG. 6 shows a perspective view of an example illuminated infusion line.
FIG. 6A shows a perspective view of a distal portion of the illuminated infusion line of FIG. 6.

FIGS. 5, 6, and 6A show alternative implementations of an illuminated infusion line without using a coupling element, such as the coupling joint 240. In these implementations, the infusion line is a single flexible elongate member that carries an optical fiber. FIG. 5 illustrates another example implementation of an illuminated infusion line 510 in situ in an eye 520. The illuminated infusion line 510 includes an infusion arrangement 511 having the flexible elongate member 516 that is configured to carry an infusion fluid via a lumen 518 defined by the flexible elongate member 516. The infusion arrangement 511 also includes an optical fiber 514 that extends through the lumen 518. The infusion arrangement 511 additionally includes a flow tube 512 configured to penetrate the eye 520, such as the sclera 522 of the eye 520, and deliver fluid and light, via the optical fiber 514, to the posterior segment 524. In some implementations, the optical fiber 514 is freely movable or free-floating within the lumen 518 of the flexible elongate member 516. In other implementations, the optical fiber 514 is directly or indirectly coupled to a wall of the lumen 518, such as by mechanical attachment, adhesive, and/or other desired or suitable coupling mechanism. During a surgical procedure, the optical fiber 514 may transmit light to a surgical field while in contact with fluid being delivered into the eye 520. In that regard, the optical fiber 514 may extend through the flow tube 512 into the posterior segment 524 as the flow tube 512 provides fluid to the posterior segment 524.

As can be seen in FIG. 5, the optical fiber 514 illuminates the field of view or region 526. The field of view 526 illuminated by the light emitted by the optical fiber 514 spans an angle α. In various implementations, the angle α may have a value between approximately 30 degrees and approximately 150 degrees, between approximately 30 degrees and approximately 120 degrees, between approximately 30 degrees and approximately 90 degrees, and/or other desired or suitable values. Thus, some implementations may be used to provide a larger range of illumination, while other implementations may be used to provide a smaller range of illumination. In other instances, the optical fiber 514 may be configured to provide targeted illumination for a narrower field of view. In such implementations, the angle α may have a value between approximately 1 degree and approximately 30 degrees, between approximately 10 degrees and approximately 30 degrees, between approximately 20 degrees and approximately 30 degrees, and/or other desired or suitable values.

FIGS. 6 and 6A illustrate a distal portion of another example illuminated infusion line 600. This illuminated infusion line 600 is similar in many respects to the infusion line 510 in FIG. 5, and for ease of reading, similar features will not be re-described in detail. The illuminated infusion line 600 includes an infusion arrangement 611 having a flow tube 630 and a flexible elongate member 610. The flexible elongate member 610 defines a lumen 612. An optical fiber 622 extends along the illuminated infusion line 600. In some instances, the optical fiber 622 may be disposed within at least a distal portion of the lumen 612. In some instances, the optical fiber 622 may extend entirely or substantially entirely through the lumen 612. Thus, in some instances, the lumen 612 is thus configured to carry the optical fiber 622 and the fluid to be delivered into the eye via the flow tube 630. In that regard, the flexible elongate member 610 and the flow tube 630 may be structurally arranged such that the fluid flows and/or the optical fiber 630 extends between the lumen 612 and a lumen 625 of the flow tube 630.

In some implementations, the optical fiber 622 may be separate or remote from the flexible elongate member 610 along a portion of a length of the illuminated infusion line 600. For example, in some instances, the optical fiber 622 may be separate or remote from the flexible elongate member along a proximal portion of the illuminated infusion line 600 (e.g., a portion of the illuminated infusion line disposed nearer to a fluid source and/or a light source). Thus, in some implementations, the optical fiber 622 may be disposed within the flexible elongate member 610 for only a portion of the length of the illuminated infusion line 600. For example, the optical fiber 622 may be disposed with the lumen 612 of the flexible elongate member 610 along the distal portion of the illuminated infusion line 600. In other implementations, the optical fiber 622 may be disposed within the lumen 612 of the flexible elongate member 610 at or near a fluid source and/or a light source. That is, the optical fiber 622 may be disposed within the lumen 612 the flexible elongate member 610 for substantially the entire distance between the light source/fluid source and the surgical field. In other instances, the optical fiber 622 may be embedded within the material forming the flexible elongate member 610 for all or a portion of the length of the flexible elongate member 610. For example, the optical fiber 622 may be disposed in a cavity or passage formed in the flexible elongate member 610 that is separate and/or isolated from the lumen 612.

FIG. 6A illustrates the distal end of the illuminated infusion line 600. The optical fiber 622 is disposed within the lumen 625 of the flow tube 630. For example, the optical fiber 622 may extend along an inner wall 631 of the lumen 625. In that regard, the optical fiber 622 may be attached or otherwise coupled to the inner wall 631, such as, for example, by mechanical coupling, an adhesive, or in any other attachment manner. In other implementations, the optical fiber 622 may be disposed freely within the flow tube 630.

Figures 8, 8A:
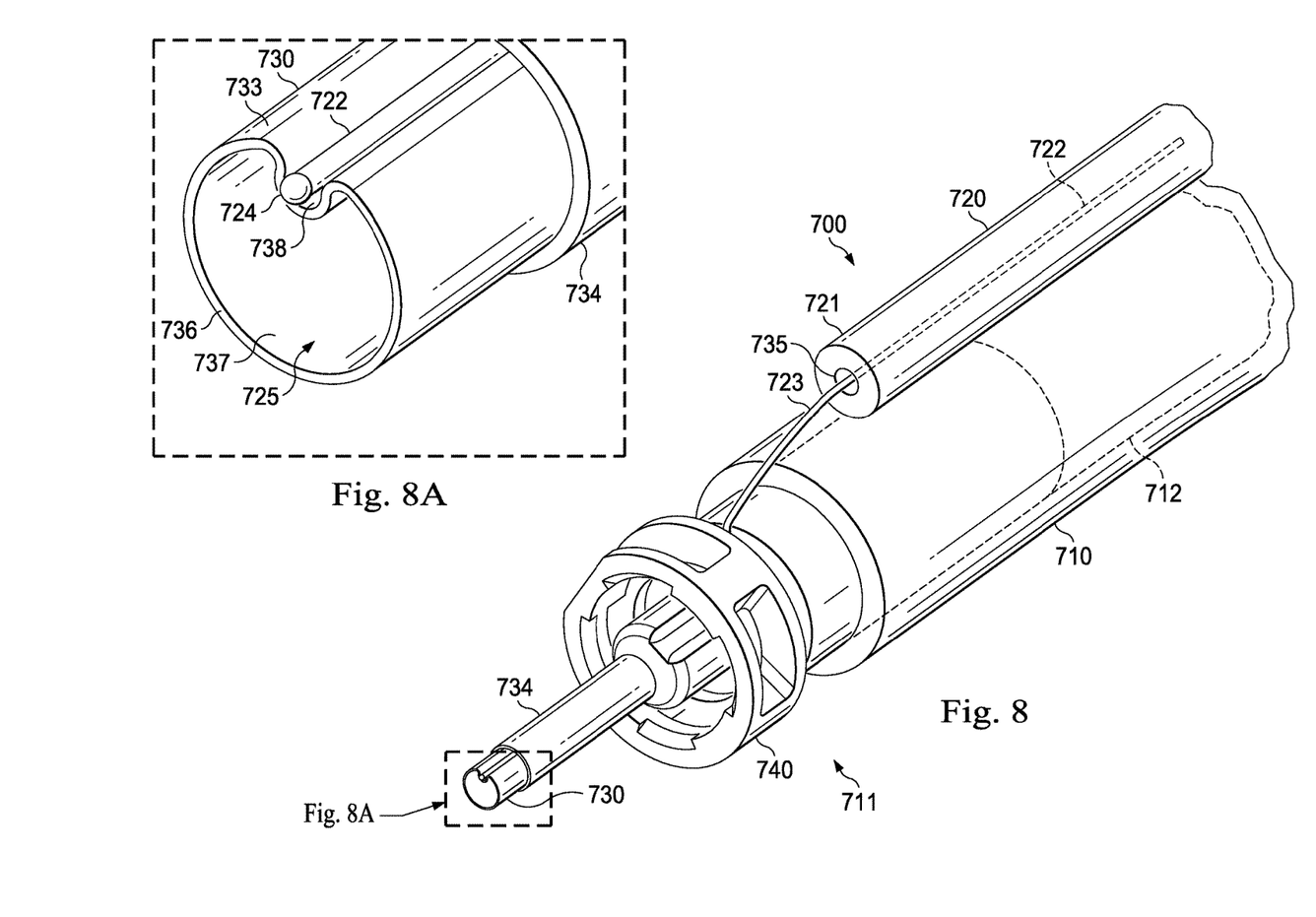
FIG. 8 shows a perspective view of an example illuminated infusion line.
FIG. 8A shows a perspective view of a distal portion of the illuminated infusion line of FIG. 8.

The distal tip 624 of the optical fiber 622 may be situated relative to a distal tip 632 of the flow tube 630 to illuminate the interior of the eye. In the implementation illustrated in FIG. 6A, the distal tip 624 extends distally beyond the distal tip 632 of the flow tube 630. In other implementations, the distal tip 624 of the optical fiber 622 may be positioned proximally of the distal tip 632 of the flow tube 630. In still other instances, the distal tip 624 of the optical fiber 622 may be aligned with the distal tip 632 of the flow tube 630. Further, the size and shape of the distal tip 624 of the optical fiber 622 may vary in different implementations. For example, as shown in FIG. 6A, the distal tip 624 may be tapered. Alternatively, the distal tip 624 may also be spherical or ball-shaped, as illustrated in FIG. 8A. In still other implementations, the distal tip 624 may have other suitable or desired sizes or shapes. The size and shape of the distal tip 624 of the optical fiber 622 and/or its position relative to the distal tip 632 of the flow tube 630 may be selected to achieve a desired illumination within the surgical field, such as the desired illumination angle α (as described with respect to FIG. 5).

Figure 7:
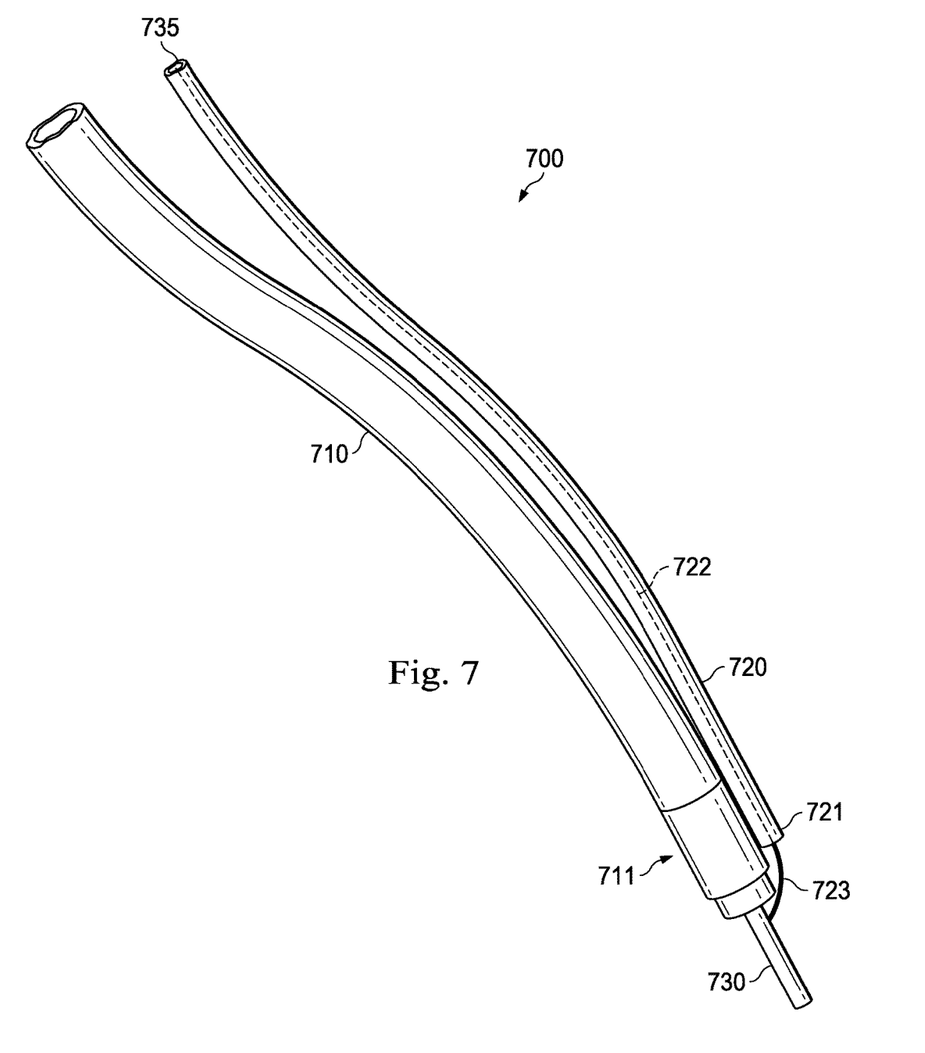
FIG. 7 shows an example illuminated infusion line.

FIGS. 7, 8, and 8A illustrate another example illuminated infusion line, referenced herein by the number 700. In some implementations, the optical fiber of the illuminated infusion line may be surrounded by one or more protection layers. This protection layer may include one or more of the flexible elongate members described herein. Alternately or in combination, the protection layer may include a coating or sheath applied or otherwise disposed directly on the optical fiber that is distinct from the flexible elongate members described herein. The protection layer may reduce the likelihood of damage to the optical fiber that results from directly contacting another component, such as the flow tube or a trocar cannula.

The ophthalmic illumination infusion line 700 includes an optical fiber 722 and an infusion arrangement 711. The infusion arrangement 711 includes a flexible elongate member 710 for passing infusion fluid, a flexible elongate member 720 that defines a lumen 735, and a flow tube 730 configured to penetrate tissue and provide illumination and infusion fluid to a surgical site. The optical fiber 722 extends through the lumen 735 and is protected by the flexible elongate member 720. Here, the optical fiber 722 includes an additional protection layer 723. The protection layer 723 may protect the optical fiber 722 while coupled to the flow tube 730 or disposed within the flexible elongate member 720. The protection layer 723 may also protect the optical fiber 722 in the transition area between a distal end 721 of the flexible elongate member 720 and the flow tube 730.

With reference to FIGS. 8 and 8A, a lumen 725 of the flow tube 730 is in fluid communication with a lumen 712 of the flexible elongate member 710. The optical fiber 722 extends through the lumen 735 of the flexible elongate member 720. In some implementations, the flexible elongate member 720 may extend substantially parallel to the flexible elongate member 710. In some implementations, the flexible elongate members 710 and 720 may be spaced apart from one another, while in other implementations the flexible elongate members 710 and 720 are adjacent to one another. In some implementations, the flexible elongate members 710 and 720 are attached to one another to facilitate ease of manipulation. For example, the flexible elongate members 710 and 720 may be coupled to each other, for example, by mechanical coupling, an adhesive, a wrapping or sheath, or by other arrangement. In some implementations, the flexible elongate members 710 and 720 may be covered by a sheath such that the user need only physically handle one conduit. FIG. 8 shows a guard 740 positioned proximally of the flow tube 730. The guard 740 may facilitate proper positioning of the illuminated infusion line 700 relative an eye or to a cannula disposed in an eye. A cannula may extend through the sclera of an eye and provide a passage through which the flow tube 730 may be inserted, thereby permitting introduction of the flow tube 730 into an interior of the eye. Use of a cannula may prevent repeated trauma to an eye that may result by repeated introduction and withdrawal of an instrument or device, such as an illuminated infusion line, through an incision or wound formed in an eye. A cannula may be utilized in combination with any illuminated infusion line described herein.

As best seen in FIG. 8, the optical fiber 722 may extend beyond a distal end 721 of the flexible elongate member 720. The protection layer 723 may surround the optical fiber 722 and may protect the optical fiber 722 from damage from contact with other items or materials. Protection provided by the protection layer 723 may be particularly beneficial against damage that may be caused by contact with rigid materials, such as, for example, in instances where the flow tube 730, a trocar cannula, etc., are rigid members. The protection layer 723 may also protect the optical fiber 722 in a transition area between the distal end 721 of the flexible elongate member 720 and the flow tube 730. The likelihood of damage may be greater in a transition area of the optical fiber 722, where a portion of the optical fiber 722 is exposed to the environment and is not disposed on or within another component (such as the flexible elongate members 710, 720, or the flow tube 730). An additional protection layer 734, best seen in FIG. 8, may surround all or a portion of the flow tube 730. For example, the protection layer 734 may surround a portion of the flow tube 730 that is in contact with the eye around the incision in the sclera through which the flow tube 730 is inserted or in contact with a cannula used to introduce the illuminated infusion line into the eye. The protection layer 734 may prevent the optical fiber 722 and/or the flow tube 730 from directly contacting the anatomy.

Still referring to FIGS. 8 and 8A, the optical fiber 722 may be coupled to an exterior of the flow tube 730. For example, an exterior surface 733 of the flow tube 730 may include a groove 738 that is sized and shaped to receive the optical fiber 722. In other instances, the flow tube 730 may not include a groove into which the optical fiber 722 is received. The optical fiber 722 may be affixed to the exterior surface (e.g., within the groove 738 in the illustrated implementation or otherwise in different implementations) of the flow tube 730, such as by mechanical attachment, adhesive, and/or other suitable coupling. In other implementations, a space, a groove, a channel, and/or other feature configured to receive the optical fiber 722 may be provided along an interior surface of the flow tube 730. In some instances, such a feature may be provided along an inner wall 737 of the flow tube 730. As indicated above, in some implementations, the flow tube 730 may not include a feature configured to receive the optical fiber 722, and the optical fiber 722 may be coupled directly to the exterior or interior of the flow tube 730. A distal tip 724 of the optical fiber 722 may be positioned proximal to, aligned with, and/or extend distally beyond a distal tip 736 of the flow tube 730 in various implementations. The distal tip 724 may be sized and shaped in any of a variety of different implementations to facilitate the desired transmission of light to the surgical field. In some instances, as shown, the distal tip 724 is ball-shaped or spherically-shaped. However, the tip may be shaped differently in other implementations. For example, as shown in FIG. 6A, the distal tip of the optical fiber may be tapered. In still other instances, the distal tip of the optical fiber may be flat. However, the distal tip of the optical fiber may have any desired shape or configuration.

Figure 9:
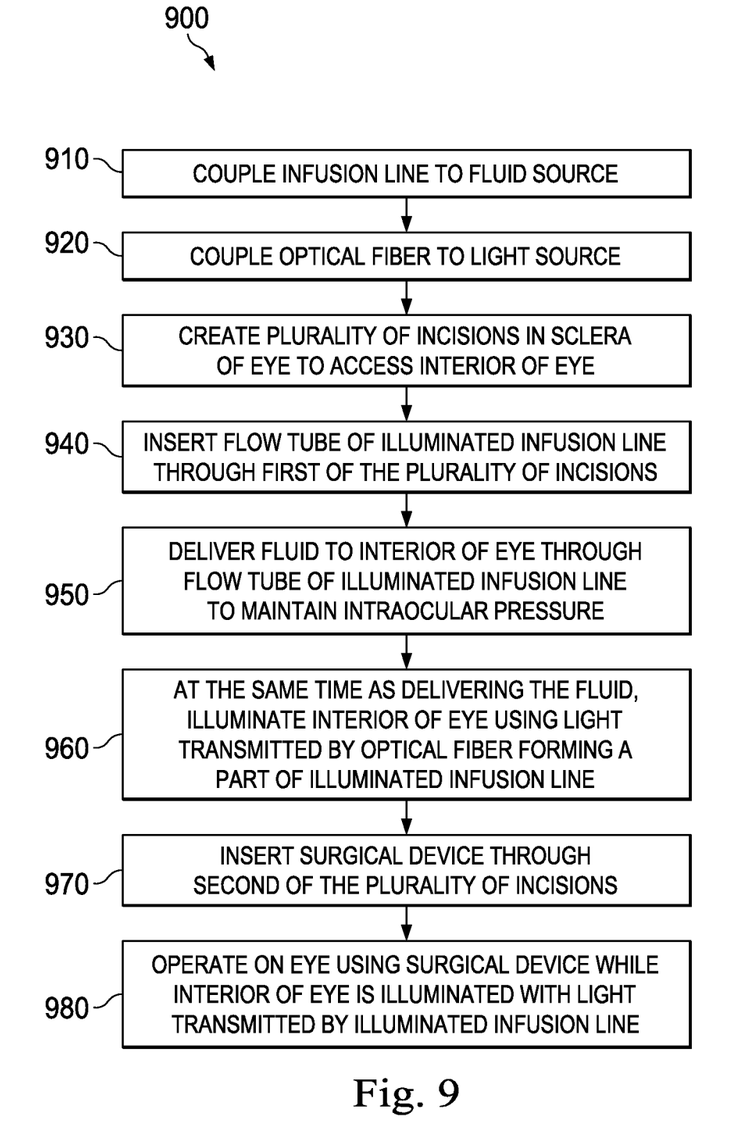
FIG. 9 is an example flowchart illustrating a method of performing an ophthalmic surgical procedure.

FIG. 9 illustrates a flow diagram of an example method 900 of performing an ophthalmic surgical procedure. As illustrated, the method 900 includes a number of enumerated steps, but implementations of the method 900 may include additional steps before, after, and in between the enumerated steps. In some implementations, one or more of the enumerated steps may be omitted or performed in a different order.

At step 910, the method 900 includes coupling an illuminated infusion line to a fluid source. At step 920, the method 900 includes coupling an optical fiber of the illuminated infusion light to a light source. For example, as illustrated in the example shown in FIG. 1, the flexible elongate member 114 of the illuminated infusion line 110 may be coupled to the fluid source 144. The optical fiber 118 may be coupled to the light source 146. In some implementations, the fluid source and/or the light source may be integrated in a surgical console (e.g., the console 141 of FIG. 1). In such implementations, coupling the illuminated infusion line or a flexible elongate member thereof to a fluid source may include coupling the illuminated infusion line or the flexible elongate member to the surgical console. Similarly, coupling the optical fiber to a light source may include coupling the optical fiber to the surgical console.

At step 930, the method 900 includes forming one or more incisions in the sclera of the eye to access an interior of the eye. The user may create the one or more incisions through the sclera in the pars plana using a trocar, for example. The incision is called a sclerotomy. A trocar blade may then be removed, with the trocar cannula remaining within the incision and defining a lumen into the posterior segment of the eye. The user may view the eye during the surgical procedure using a surgical microscope. A light source of the surgical microscope may provide the illumination for use by the surgeon during the step 930. This light source may provide illumination prior to the illuminated infusion line being inserted into the eye. In various implementations, one, two, three, four, or more incisions may be made during the step 930. Various surgical devices, such as an operating probe (aspiration probe, cutting probe, vitrectomy probe, etc.), illuminator, and/or infusion line may be inserted into the posterior segment via the one or more incisions. In some implementations, at least three incisions (e.g., one each for the operating probe, illuminator, and infusion line) may be made at the same time, at the beginning of the surgical procedure. In some implementation, only two incisions are made. For example, one incision may be formed for the illuminated infusion line, and one incision may be formed for a surgical device. Reducing the number of incisions may reduce the risk of harm to the patient during and after the surgery.

At step 940, the method 900 includes inserting a flow tube of the illuminated infusion line through a first of the plurality of incisions. In some implementations, prior to insertion of the flow tube, a cannula may be inserted into the incision. As explained above, the cannula permits repeated insertion and removal of a device, such as the flow tube, into an out of the eye without causing additional trauma to eye or otherwise further enlarging the incision or damaging the tissues surrounding the incision. For example, as shown in the example of FIG. 1, the flow tube 112 of the illuminated infusion line 110 (FIG. 1) penetrates the eye, as the flow tube 112 is inserted into the posterior segment. The flow tube may be in fluid communication with the fluid source. Thus, at step 950, the method 900 includes delivering fluid into the interior of the eye through the flow tube. The fluid may be delivered to the eye in order to maintain intraocular pressure within the eye. As shown in the example of FIG. 1, fluid from the fluid source 144 may be provided to a lumen of the flexible elongate member 114 and then to the flow tube 112 to be delivered into the eye 120. The flow tube may also be coupled to the optical fiber. Thus, at step 960, the method 900 includes illuminating the interior of the eye using light transmitted by the optical fiber. As shown in the example of FIG. 1, light from the light source 146 may be provided to the optical fiber 118 to illuminate the surgical field within the eye 120. In some instances, the steps 950 and 960 may be performed simultaneously. Thus, in some implementations, the illuminated infusion line may illuminate the interior of the eye at the same time as the illuminated infusion line delivers fluid to the interior of the eye to maintain intraocular pressure.

At step 970, the method 900 includes inserting a surgical device through a second of the plurality of incisions in the sclera. As shown in the example of FIG. 1, the surgical device 130 may be inserted through the sclera 122 and into the posterior segment of the eye 120. The shadows generated within the eye may be minimized as the surgical device is inserted into the eye as a result of the light being provided by the illuminated infusion line. An advantageous position for the infusion line may be selected such that the shadows within the surgical field are minimized. At step 980, the method 900 includes operating on the eye using the surgical device while the interior of the eye is illuminated with light transmitted by the optical fiber. Again, as illustrated in the example shown in FIG. 1, the surgical device 130 may be used to cut or aspirate tissue within the eye. The surgeon may view the surgical field using light provided by the illuminated infusion line.

Persons of ordinary skill in the art will appreciate that the implementations encompassed by the present disclosure are not limited to the particular exemplary implementations described above. In that regard, although illustrative implementations have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

Although the various figures, examples, and implementations described herein show or are described as having a particular combination of features, other implementations are also contemplated that include a subset of or all of the features disclosed herein. Further, it is specifically contemplated that features described in the context of one or more implementations may be added to other implementations. Also, in some instances, not all of the features described in relation to one or more implementations are required for other variations of those implementations.

What is claimed is:

1. An ophthalmic surgical system, comprising:
   a light source;
   a fluid source;
   an illuminated infusion line comprising:
      an infusion arrangement comprising:
         a first flexible elongate tube defining a first lumen;
         a second flexible elongate tube defining a second lumen; and
         a flow tube coupled to a distal end of the first flexible elongate tube, the flow tube defining a third lumen and comprising a groove on an exterior surface thereof, the first lumen and the third lumen in fluid communication with the fluid source and configured to deliver a fluid from the fluid source to an interior of an eye of a patient during a surgical procedure, and the flow tube being sized to penetrate the eye of the patient and deliver the fluid to the interior of the eye; and
      an optical fiber comprising:
         a proximal portion disposed in the second lumen of the second elongate tube; and
         a distal portion received within the groove of the flow tube,
      the optical fiber being in optical communication with the light source and coupled to the infusion arrangement, the optical fiber being configured to transmit light from the light source to illuminate the interior of the eye during the surgical procedure.

2. The system of claim 1, wherein at least one of the light source and the fluid source is integrated into a surgical console.

3. The system of claim 1, wherein the light source is configured to transmit at least one of laser light, white light, red light, blue light, green light, visible light, near infrared light, or infrared light.

* * * * *